(12) United States Patent
Horie et al.

(10) Patent No.: US 7,745,181 B2
(45) Date of Patent: Jun. 29, 2010

(54) PROCESS FOR PRODUCING YEAST-DERIVED GLUCAN

(75) Inventors: Shuji Horie, Izumo (JP); Hideyuki Matsuda, Matsue (JP); Takumi Suizu, Shimane-ken (JP); Masatoshi Sakamoto, Tokyo (JP)

(73) Assignee: Alpron Co., Ltd., Minato-ku (JP)

( * ) Notice: Subject to any disclaimer, the term of this patent is extended or adjusted under 35 U.S.C. 154(b) by 882 days.

(21) Appl. No.: 11/496,741

(22) Filed: Jul. 31, 2006

(65) Prior Publication Data

US 2007/0004013 A1   Jan. 4, 2007

Related U.S. Application Data

(63) Continuation of application No. PCT/JP2004/001592, filed on Feb. 13, 2004.

(51) Int. Cl.
*C12N 1/00* (2006.01)
*C12P 1/02* (2006.01)
*C12P 19/00* (2006.01)
*C12P 19/04* (2006.01)

(52) U.S. Cl. .................... 435/101; 435/171; 435/255.1; 435/259

(58) Field of Classification Search ........................ None
See application file for complete search history.

(56) References Cited

U.S. PATENT DOCUMENTS 6,333,399 B1   12/2001   Teslenko et al.

FOREIGN PATENT DOCUMENTS

| JP | 09-322795 A1 | 12/1997 |
| JP | 09-512708 A1 | 12/1997 |
| JP | 11-500159 A1 | 1/1999 |
| JP | 11-508772 A1 | 8/1999 |
| JP | 2000-166585 A1 | 6/2000 |
| JP | 2002-209598 A1 | 7/2002 |
| JP | 2003-000197 A1 | 1/2003 |
| WO | WO 95/30022 | 11/1995 |
| WO | WO 97/02356 A1 | 1/1997 |

OTHER PUBLICATIONS

Tsuchiya, Katsura, "*Functional Waters: Acidic Electrolyzed Water and Alkaline Electrolyzed Water*," Bulletin of Science and Engineering, Takushoku University, vol. 8, No. 3, pp. 73-78 (2002).

*Primary Examiner*—David M. Naff
*Assistant Examiner*—Debbie K Ware
(74) *Attorney, Agent, or Firm*—Burr & Brown

(57) ABSTRACT

It is an object of the invention to provide a process for easily producing a glucan, which assures a high degree of safety and which does not generate an oxidation off-flavor, without using a hydroxide of an alkali metal such as sodium hydroxide. In a process of the present invention, a physically pulverized yeast is autolyzed with an intracellular enzyme thereof, in an electrolyzed alkaline water which is obtained by electrolyzing water.

19 Claims, 5 Drawing Sheets

Enzyme-treatment (two hours)

Enzyme-treatment (four hours)

β—glucan (EXAMPLE 2)

β—glucan (commercially available product)

β-glucan (EXAMPLE 2)

Wavenumber/cm$^{-1}$

Standard product

A: β-(1,3)-glucan
B: β-(1,6)-glucan
C: Glucan which is extructed from a brewer's yeast
D: Cell wall of a baker's yeast

PROCESS FOR PRODUCING YEAST-DERIVED GLUCAN This application is a continuation of the International Application No. PCT/JP2004/001592, filed Feb. 13, 2004, the entireties of which are incorporated herein by reference.

TECHNICAL FIELD

The present invention relates to a process for producing a yeast-derived glucan. In particular, the present invention relates to a process for producing a β-glucan which is a polysaccharide, from a yeast cell wall, by using, as a treatment medium, an electrolyzed alkaline water obtained by electrolyzing water.

BACKGROUND ART

A β-glucan is a substance, of which components of saccharides are polymerically bonded. There is reported that the β-glucan exhibits many physiological actions such as an action to improve an immune strength, antitumor action, cholesterol-lowering action, antiviral action, and an action to improve the number of leukocytes. In recent years, the β-glucans attract attentions as health foods, medicaments, and so on.

The above-described β-glucan is included in a cell wall of a yeast. There have been proposed many varied processes for obtaining the polysaccharide such as the β-glucan. For instance, in JP-A-2003-197, there is disclosed a process for obtaining a composition including a polysaccharide which comprises a lot of intact β-glucan, which is biologically highly active, by bacteriolyzing a yeast by effecting a protease, in particular, an enzyme agent, of which total glucanase activity is especially little. In addition, JP-A-2002-209598 proposes a process for obtaining a soluble polysaccharide, which consists of the steps of: physically pulverizing a yeast by using a high pressure homogenizer; autolyzing the yeast; and causing an action of a cell-wall digesting enzyme on a fraction of a rinsed yeast cell wall. There is disclosed that a soluble polysaccharide including a lot of β-glucan can be produced in high yield.

Further, in JP-A-11-508772, there is disclosed a process for obtaining a β-glucan-mannan preparation by separating a solid content from a product, which is obtained by autolyzing a germ cell at a pH of 5~6 and at a temperature of 35° C.~60° C. for 6~48 hours. In addition, in JP-A-11-500159, there is disclosed a process for preparing a chitosan-glucan complex. In this process, the chitosan-glucan complex is prepared by a partial deacetylation, which consists of the steps of: treating a bacteria, which comprises a chitin, with an alkali solution; treating thus obtained product with a dilute mineral acid; and further treating the product with an alkali solution having a high alkalinity.

In JP-A-9-512708, there is disclosed a process for preparing an insoluble β-(1-3)-glucan particle by treating a yeast cell which comprises a glucan, by respectively using a suitable water-soluble alkali solution for extraction, an acid for hydrolysis, and an ethanol, etc. Further, in JP-A-9-322795, there is disclosed that a solution containing a microorganism fungus body, which has, as a component thereof, a water-insoluble glucan such as a yeast is treated with an oxide having a predetermined concentration and with a hydroxide which adjusts a pH of the solution to 10~12.5, simultaneously. JP-A-9-322795 explains that this process simultaneously realizes cell destruction, bleaching, and viscosity drop of a producing microorganism. Accordingly, the water-insoluble glucan can be effectively purified.

However, above-described processes for obtaining the glucan by using an alkali, an acid, and an organic solvent, there are needed treatments such as neutralization and demineralization, which make the processes of the production complicated. In addition, if the products are provided as foods, these processes leave an anxiety in relation to a safety of the products. Moreover, these processes are not preferable in terms of the yields, either. Further, in the process in which an enzyme agent is used, there is an anxiety that the glucan may be degraded with amylase, etc., included in the enzyme agent, which leads to a problem that it is difficult to obtain a highly effective long chain glucan. Further, there cannot be sufficiently removed lipid in the yeast cell of the glucan obtained by the above-mentioned processes, so that there is an anxiety that the obtained product may be colored by an oxidation of the lipid, or an oxidation off-flavor may be generated.

DISCLOSURE OF THE INVENTION

The present invention has been developed in the above-explained background. It is therefore an object of the invention to provide a process for easily producing a glucan, which assures a high degree of safety and which does not generate an oxidation off-flavor, without using a hydroxide of an alkali metal such as sodium hydroxide.

As a result of an extensive research made by the inventors of the present invention, it has been found that there can be advantageously produced the glucan which will not be colored by oxidation and which does not generate the oxidation off-flavor, by using, as a medium, an electrolyzed water (water that has been restructured as a result of electrolysis) which is obtained by electrolyzing a tap water, especially an alkaline water produced at a cathode side (hereinafter referred to as "electrolyzed alkaline water"), at a time of autolyzing a physically pulverized yeast with an intracellular enzyme thereof, or degrading a protein by adding an enzyme to the protein.

The present invention was made on the basis of the finding indicated above. It is therefore a principle of the present invention to provide a process for producing a yeast-derived glucan, characterized in that a physically pulverized yeast is autolyzed with an intracellular enzyme thereof, in an electrolyzed alkaline water which is obtained by electrolyzing water, while the yeast is enzyme-treated by adding an alkaline protease to the yeast.

In short, in the process for producing a yeast-derived glucan according to the present invention, a physically pulverized yeast is autolyzed with an intracellular enzyme thereof, and simultaneously enzyme-treated (degradation treatment of protein) by adding an alkaline protease to the yeast, in the electrolyzed alkaline water. Accordingly, a detergent effect or a surface activity caused by the electrolyzed alkaline water is advantageously exhibited, as well as a protein component which constitutes the yeast cells is effectively degraded. Therefore, a lipid and other unnecessary components in the yeast cell are effectively dissolved in the electrolyzed alkaline water or are emulsified, whereby there is preferably separated the lipid or the other unnecessary components from the intended glucan. In this way, the components other than the glucan are eluted in the electrolyzed alkaline water, so that the protein, the lipid, and the other components are effectively removed from the glucan, which remains as a solid content, whereby a purity of thus obtained glucan is enhanced.

Also, the electrolyzed alkaline water exhibits an alkalinity, and has a low oxidation-reduction potential and a reducing power, so that there is not caused an oxidation etc. of the lipid during processing of the glucan. Therefore, there is advantageously restricted or prevented the coloration or a generation of the oxidation off-flavor caused by the oxidation of the lipid. Further, by using the electrolyzed alkaline water, there is enhanced a protease activity in an intracellular enzyme, and there is effectively restricted an amylase activity, whereby there can be obtained the glucan which has a chain longer than that of an ordinary glucan, although mechanism of this effect has not been revealed.

Moreover, although the electrolyzed alkaline water exhibits the alkalinity, there is not used a hydroxide of an alkali metal such as a sodium hydroxide. For this reason, there is not needed any troublesome treatment of the neutralization or the demineralization, so that there can be produced the glucan more easily, compared with the conventional processes, and there is no problem in thus obtained glucan in terms of its safety as a food.

In addition, the present process is executed by a combination of the autolysis of the yeast with the intracellular enzyme thereof and the enzyme-treatment of the yeast with the alkaline protease, so that a more effective degradation reaction can be conducted, compared with a process in which only one of the treatments is independently conducted. Also, there can be reduced the amount of the alkaline protease to be added, compared with a process in which the yeast is only enzyme-treated, so that the production cost can be lowered. In addition, a development of an allergy, which is caused by the addition of the enzyme, is advantageously prevented, which highly assures a quality of thus obtained glucan.

In one preferred form of the process for producing the yeast-derived glucan according to the present invention, there is advantageously adopted a constitution wherein the yeast is physically pulverized in the electrolyzed alkaline water which is obtained by electrolyzing water. Accordingly, oxidation of a component of the yeast cell can be significantly and effectively prevented.

In another preferred form of the process for producing the yeast-derived glucan according to the present invention, the process is characterized by comprising the steps of: preparing a mixture by adding a yeast and an alkaline protease to an electrolyzed alkaline water and mixing thereof, wherein the alkaline water is obtained by electrolyzing water; physically pulverizing the yeast in thus obtained mixture; and autolyzing the yeast with an intracellular enzyme thereof, and simultaneously enzyme-treating the yeast with the alkaline protease. In still another preferred form of the process for producing the yeast-derived glucan according to the present invention, the process is characterized in that an alkaline protease is added to a yeast in an electrolyzed alkaline water which is obtained by electrolyzing water, immediately after the yeast is physically pulverized, so that autolysis of the yeast with an intracellular enzyme thereof and enzyme-treatment by adding the alkaline protease to the yeast are simultaneously effected.

In these preferred forms of the process for producing the yeast-derived glucan according to the present invention, there can be advantageously produced the glucan, which assures a high degree of safety and does not generate the oxidation off-flavor. In addition, the alkaline protease, which promotes the autolysis of the yeast, is added to the yeast at an early stage of the process for the production, and the autolysis of the yeast with the intracellular enzyme thereof and the enzyme-treatment with the alkaline protease are simultaneously effected. Accordingly, the protein in the yeast cell can be degraded in a shorter period of time, by a synergistic effect of the autolysis and the enzyme-treatment, so that there can be advantageously realized a reduction of the time for the production.

In still another preferred form of the process for producing the yeast-derived glucan according to the present invention, a pH of the electrolyzed alkaline water is within a range of 8.5~11.5. By adopting the pH within this range, there is advantageously realized the autolysis of the yeast with the intracellular enzyme and the enzyme-treatment of the yeast with the alkaline protease, while the protein can be easily solubilized in the medium, whereby the glucan, which has an enhanced purity, can be produced.

In still another preferred form of the process for producing the yeast-derived glucan according to the present invention, an oxidation-reduction potential of the electrolyzed alkaline water is within a range of −100~−800 mV. Accordingly, a reducing power of the electrolyzed alkaline water is effectively activated, whereby there is advantageously prevented the oxidation of various components. In addition, there can be effectively restricted generation of oxides, which are regarded as giving an adverse effect to a human body. Therefore, there can be advantageously produced the glucan, which is safer to the human body and has excellent effects.

BRIEF DESCRIPTION OF THE DRAWING

FIGS. 1a and 1b are figures showing results of SDS-PAGE in EXAMPLE 1, wherein FIG. 1a shows results after two hours of the enzyme-treatment, while FIG. 1b shows results after four hours of the enzyme-treatment, wherein degrees of strength of blue color of the gel are indicated by the number of "+", together with photographs of the gel after the electrophoresis.

FIGS. 2a and 2b are photographs of the β-glucan, wherein FIG. 2a shows the β-glucan produced in EXAMPLE 2, while FIG. 2b shows a commercially available β-glucan.

BEST MODE FOR CARRYING OUT THE INVENTION

Figure 1A:
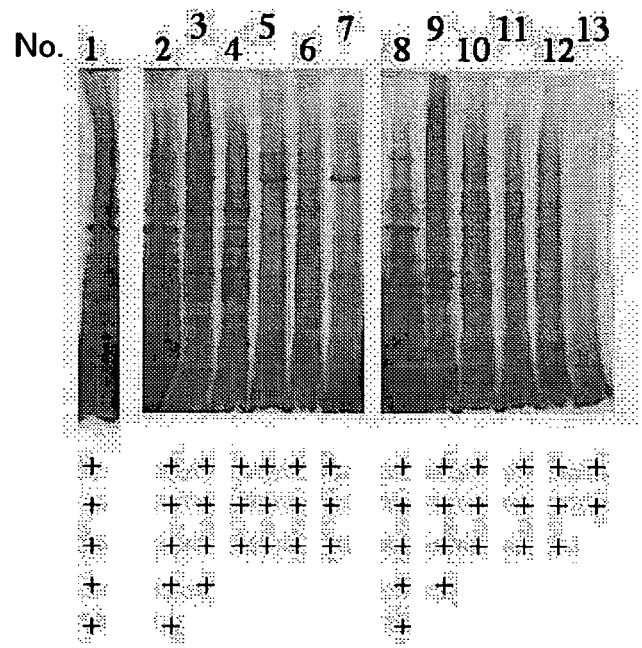

The yeast adopted to the present invention is not particularly limited. For example, there can be advantageously used at least one of a brewer's yeast, a sake yeast, a wine yeast, a baker's yeast, a soy sauce yeast, and a miso yeast, which are yeasts of Saccharomyces and are generally used for brewing a liquor, producing an alcohol, or breadmaking. These yeasts are commercially available, and the baker's yeast and the brewer's yeast are commercially available as dry yeasts, for instance.

The glucan is manufactured by extracting a water-insoluble glucan contained in the yeast, by autolyzing and enzyme-treating the physically pulverized yeast. The present invention is characterized in that the electrolyzed alkaline water obtained by electrolyzing water is used as the medium for the autolysis and the enzyme-treatment.

In detail, the electrolyzed water is obtained by electrolyzing water, such as an ordinary tap water, in an electric cell having a diaphragm. Due to this electrolysis, each of ions contained in the water is moved to an electrode having a charge, which is opposite to that of the ion, so that there are collected cations at a cathode side of the electrolysis apparatus, and then hydrogen is generated at the cathode side. Accordingly, there is produced water, which has a higher pH and a higher concentration of cation, compared with a tap water (raw water), and has an ability to achieve a reduction. Meanwhile, at an anode side, there are collected anions, and oxygen is generated. Accordingly, there is produced water, which has a lower pH and a higher concentration of anion, compared with a tap water (raw water), and has an oxidizable property. As explained above, there are two kinds of electrolyzed water, and in the present invention, there is used the electrolyzed alkaline water, which is generated at the cathode side.

The electrolyzed alkaline water to be used is not particularly limited, as long as it is an electrolyzed water produced at the cathode side by the electrolysis as described above. However, it is desirable that a pH of the electrolyzed alkaline water is 8.5~11.5, more preferably 9.5~10.5. This is because, if the pH is lower than the above-mentioned range, there is an anxiety that a solvent action of the protein may not be preferably exhibited. In addition, if the pH is higher than the above-mentioned range, there is an anxiety that the pH is far beyond the optimum pH of the enzyme so that the activity of the enzyme may be lost.

In the electrolyzed alkaline water, there is dissolved a hydrogen gas produced at the cathode side, and a value of the oxidation-reduction potential of the electrolyzed alkaline water is lower than that of the tap water etc. (raw water) because of the hydrogen gas. The oxidation-reduction potential of the electrolyzed alkaline water is not particularly limited, either. However, it is desirable to use an electrolyzed alkaline water whose oxidation-reduction potential is −100~−800 mV, more preferably −500~−800 mV. If there is used the electrolyzed alkaline water, whose oxidation-reduction potential is low, the reducing power of the electrolyzed alkaline water is effectively activated. Accordingly, the oxidation of a substance, such as the lipid, in the yeast cell is advantageously prevented, so that the generation of the oxidation off-flavor is highly effectively restricted. In addition, and there can be obtained the glucan of a high quality, which is not colored by the oxidation, owing to a moderate reduction bleaching.

If there is used the electrolyzed acidic water, which is produced at the anode side, there is an anxiety that the quality of thus obtained glucan may be deteriorated, because: the protein cannot be sufficiently degraded; the lipid in the yeast cell may not be sufficiently solubilized; the glucan may be turned yellow because of the oxidation of the lipid which is not solubilized; or the oxidation off-flavor is generated.

In order to obtain the water-insoluble glucan from the yeast by using the electrolyzed alkaline water as described above, there may be preferably adopted the following processes, for instance.

First, the yeast is physically or mechanically pulverized or milled, in order to autolyze the yeast with the intracellular enzyme thereof. In this case, the process for pulverizing the yeast is not particularly limited, but may be suitably selected from among any known various methods of pulverization, such as a pulverization by using a ball mill or a bantam mill, or a method of ultrasonication. Conditions of the pulverization, such as the temperature and time are also suitably determined based on an amount and a kind of the yeast and a method of the pulverization etc. to be used. By the pulverization treatment, a cell wall of the yeast is pulverized, whereby various components in the cell, such as proteins, saccharides, amino acids, organic acids, and lipids, are taken out of the cell. In pulverizing the yeast, there is generally adopted a wet process, and water such as a tap water is used as a medium. However, in the present invention, it is desirable that the electrolyzed alkaline water as described above is used. If the yeast is pulverized in the electrolyzed alkaline water, the enzyme existed in the cell is eluted to the electrolyzed alkaline water, and other hydrophilic components are also solubilized.

After the above-described pulverization treatment, thus pulverized yeast is autolyzed under the presence of the electrolyzed alkaline water. In detail, if the yeast is pulverized by the wet process, in other words, if the yeast is pulverized in the electrolyzed alkaline water, the intracellular enzyme of the yeast is dissolved in the electrolyzed alkaline water including the pulverized yeast. Thereafter, if the solution is kept as it is and at a predetermined temperature, the yeast is autolyzed. Meanwhile, if the yeast is pulverized by a dry process, the yeast is autolyzed by adding a suitable amount of the electrolyzed alkaline water to the pulverized yeast and keeping the yeast at a predetermined temperature.

The amount of the electrolyzed alkaline water is not particularly limited. However, if the amount of the electrolyzed alkaline water relative to the yeast is too little, there is an anxiety that unnecessary components such as the lipid cannot be sufficiently solubilized in the the electrolyzed alkaline water. On the other hand, if the amount of the electrolyzed alkaline water is too much, there is an anxiety that the digestion with the intracellular enzyme of the yeast may not be effectively conducted, and various components such as the protein, the lipid, the saccharides (except for the glucan) cannot be degraded enough to solubilize these components. Accordingly, it is desirable that the electrolyzed alkaline water is used in an amount of 1~20 parts by weight, preferably in an amount of 2~5 parts by weight, per one part by weight of the yeast (dry weight).

Also, the treatment temperature of the autolysis is generally within a range of about 40° C.~about 70° C., so that the protein in the yeast cell and the enzymes such as the protease may not be denatured, and the action of the digestion with the intracellular enzyme of the yeast can be effectively exhibited. In the above-mentioned range of the temperature, it is especially desirable to set the temperature to about 60° C., so as to prevent a contamination by various kinds of minor germs. It is also desirable to set the temperature to about 40° C.~about 50° C., which is the optimum temperature of the intracellular enzyme of the yeast, when the treatment is conducted under aseptic conditions.

Moreover, a treatment time for the autolysis is suitably determined, considering a kind and a concentration of the enzyme, which is added for the enzyme-treatment, so that the components of the yeast cell, other than the glucan, can be sufficiently degraded. Generally, it is desirable that the treatment time is about eight hours to about 48 hours, preferably 12~24 hours. This is because, if the time for the autolysis is too long, an extended time period is required to produce the glucan, so that the efficiency of the production is deteriorated, which is not practical. In addition, it is needless to mention that the autolysis is effected only when the enzyme in the yeast cell is activated. If the time for the autolysis is too long, the enzyme may be inactivated and may not be sufficiently digested, whereby the autolysis may be in vain. Moreover, the electrolyzed alkaline water has a characteristic that if the electrolyzed alkaline water contains a lot of oxidizable materials such as an organic matter, the reduction potential and the pH tend to return to those of the raw water. Accordingly, even if the treatment time is extended, there is an anxiety that the pH and the oxidation-reduction potential of the electrolyzed alkaline water may return to those of the raw water, so that effects of the electrolyzed alkaline water cannot be obtained. On the other hand, if the time for the autolysis is too short, the digestion by the intracellular enzyme of the yeast is not sufficiently proceeded, whereby the purity of thus obtained glucan is deteriorated.

In the present invention, the yeast is also enzyme-treated by using an alkaline protease, in addition to the autolysis, in order to promote the above-described treatment of the autolysis and to obtain the glucan of a high purity. The protease to be used in this enzyme-treatment is not particularly limited, as long as the protease can degrade the protein in the electrolyzed alkaline water and assures a high degree of safety with a human body. For example, there can be exemplified "Proleser-FG-F" (available from AMANO ENZYME INC.) as the protease.

An amount of the alkaline protease to be added can be suitably determined based on a type etc. of the protease to be used. If the amount of the alkaline protease to be added is too little, there is not sufficiently realized the degradation of the protein with the alkaline protease. On the other hand, if the amount is too much, there are anxieties of developing an allergy caused by the alkaline protease and of raising a manufacturing cost. For these reasons, it is desirable that the alkaline protease is used in an amount of 0.01~2.0 parts by weight, preferably in an amount of 0.1~0.5 part by weight per 100 parts by weight of the yeast to be used (dry weight).

Also, processing conditions of the enzyme-treatment is suitably determined based on the alkaline protease to be used. As a time for the enzyme-treatment, there is generally adopted a time about one to about 48 hours, preferably about one to about 10 hours. A temperature for the enzyme-treatment is not particularly limited, as long as the temperature is within a range which allows the alkaline protease to posses an activity. However, it is desirable to adopt the optimum temperature of alkaline protease. The optimum temperature of alkaline protease is generally within a range of 45~70° C.

By the enzyme-treatment by adding the alkaline protease to the yeast as described above, there is effectively promoted the degradation of, e.g., the protein which is not solubilized in the electrolyzed alkaline water or is attached to the glucan.

The above-mentioned treatment of the autolysis and the enzyme-treatment may be effected sequencially or simultaneously. In detail, there can be adopted any one of the followings: (1) a process in which the pulverized yeast is autolyzed for a predetermined time, and then the alkaline protease is added to the yeast for the enzyme-treatment; (2) a process in which the yeast is pulverized after the yeast and the alkaline protease are added to and mixed with the electrolyzed alkaline water, and then the autolysis and the enzyme-treatment of the yeast is effected simultaneously; (3) a process in which the alkaline protease is added to the yeast immediately after the yeast is pulverized, whereby the autolysis and the enzyme-treatment are effected roughly simultaneously. It is needless to mention that the treatment temperature and time are determined based on characteristics of the intracellular enzyme of the yeast and the alkaline protease, especially when the autolysis and the enzyme-treatment are effected simultaneously, as described in the processes of (2) and (3). As the treatment temperature, there is generally preferably adopted a temperature within a range of 50~70° C. As the treatment time, it is desirable to adopt a time within a range of 12~24 hours. In the cases of the above (2) and (3), the intracellular enzyme of the yeast and the alkaline protease are simultaneously effected on the yeast. Accordingly, the protein in the yeast cell is degraded within a further reduced period of time, compared with the case of the above (1), so that the time for producing the glucan can be further reduced.

As described above, the autolysis of the yeast with the intracellular enzyme thereof is effected in combination with the enzyme-treatment by adding the protease to the yeast, so that various components, which constitute the yeast cell, in particular the protein, is effectively degraded and solubilized in the electrolyzed alkaline water.

In the present invention, there is adopted, as the treatment medium, the electrolyzed alkaline water, which is characterized by having the oxidation-reduction potential lower than that of an ordinary water and having the pH higher than that of the ordinary water. Accordingly, there is advantageously produced a long chain glucan which is water-insoluble, although the reason for this has not been sufficiently revealed. The inventors of the present invention assume that a protease activity in the intracellular enzyme is enhanced and the degradation of the protein with the protease is effectively realized, while there is restricted an activity of the enzyme which degrades the glucan in the intracellular enzyme, so that the degradation of the glucan is restricted.

In addition, the electrolyzed alkaline water is characterized by having a weaker surface tension and higher abilities of an osmosis and an emulsification. In other words, the electrolyzed alkaline water has a detergent action or a surface-active property, and the effects are advantageously exhibited. Accordingly, the lipids etc., which are components of the yeast cells, are effectively emulsified in the electrolyzed alkaline water, whereby there can be extremely preferably realized the separation between the components such as the lipids and the water-insoluble glucan.

In addition, the electrolyzed alkaline water has a low oxidation-reduction potential, so that oxidation of the components of the yeast cells is highly effectively prevented. Moreover, generation of the oxidation off-flavor and coloration of the glucan caused by the oxidation can be effectively prevented.

After the autolysis and the enzyme-treatment as described above are completed, there is executed a predetermined heat-treatment. Due to the heat-treatment, various enzymes are inactivated, and the degradation reaction of the various components by the enzyme is completed. Conditions of the heat-treatment are not particularly limited, and generally used conditions of the heat-treatment can be adopted. Usually, the enzymes in the electrolyzed alkaline water are inactivated by a heat-treatment at about 80 to about 100° C. for about five to about 60 minutes.

Thereafter, the electrolyzed alkaline water, of which various unnecessary components have been eluted, is separated and removed by a solid-liquid separation such as centrifugation or filtration. For instance, the electrolyzed alkaline water, in which the glucan is dispersed, is centrifuged and a supernatant thereof is removed, so that unnecessary components are separated and removed, whereby a solid content comprising the glucan is taken out. Thus obtained solid content is subjected to a washing treatment and a drying process, as needed, whereby intended β-glucan is produced.

In the above washing treatment, it is desirable to use the electrolyzed alkaline water. This is because, if the solid content is cleaned with the electrolyzed alkaline water, components, such as lipids, which are remaining in the solid content, are more effectively removed, compared with a treatment in which an ordinary water is used, owing to a washing effect of the electrolyzed alkaline water. Therefore, the purity of the glucan, which is obtained by using the electrolyzed alkaline water is more advantageously enhanced. In addition, by using the electrolyzed alkaline water, the washing treatment can be done while the solid content is at its reduced state. Therefore, there can also be prevented a deterioration of the product caused by the oxidation during the washing treatment. The washing treatment is conducted by rinsing the solid content with a medium such as the electrolyzed alkaline water. The number of times of the washing treatment is suitably selected, but it is desirable that the washing treatment is conducted one to eight times.

In the thus obtained yeast-derived glucan, there are assured an enhanced purity, and there is advantageously restricted or prevented the generation of the oxydation off-flavor or the coloration caused by the oxidation, as described above. Moreover, the degradation of the glucan itself is restricted, so that the obtained glucan is a long chain glucan, which has good effects of improving immunity.

In the above-described process for producing the yeast-derived glucan, there is used the electrolyzed water which exhibits alkaline property, but there is not used any hydroxides of the alkali metal, such as sodium hydroxide. Accordingly, there are not needed troublesome processes of neutralization and demineralization, and the glucan can be easily produced. In addition, there can also be obtained an advantage that thus obtained glucan assures sufficient safety as a food.

Therefore, the yeast-derived glucan (β-glucan) produced according to the present invention is advantageously used as a health food, a medicament, and so on, similar to a known β-glucan.

EXAMPLES

There will be described some examples of the present invention to further clarify the present invention. However, it is needless to mention that the present invention is not limited to the details of the following examples and the presently preferred embodiment described above, but may be embodied with various changes, modifications and improvements, which may occur to those skilled in the art, without departing from the scope of the present invention.

First, there were prepared the electrolyzed water and the yeast, and the following Examples 1~5 were executed.

-Electrolyzed Water-

There were produced an electrolyzed water from a tap water of Matsue City, by using an electrolyzed water generator ("HOX-40A") available form Hoshizaki Electric Co., Ltd. As conditions of the electrolysis, there were adopted an electrolysis intensity of 3~4 (ampere) and a flow rate of 3~4 L/min. Oxidation-reduction potentials of thus obtained electrolyzed water were about +580 mV for an electrolyzed acidic water and about −700 mV for an electrolyzed alkaline water.

-Yeast-

As the yeast plant, there was prepared a dry yeast ("Super Camellia Dry Yeast" available from Nisshin Flour Milling Inc.) which is commercially available as a baker's dry yeast for home use.

Example 1

1-1) Treatment for Pulverizing Yeast Cells

Yeast cells were pulverized by a method using a beads cell disrupter. In detail, at first 0.05 g each of the dry yeast was measured and put in each tube of Sample Nos. 1~13 for the cell pulverization. Then, 0.5 ml of mediums as shown in TABLE 1 below was added to each of the tubes, and concentration of the yeast in each of the tubes was adjusted to 10 w/v %. Thereafter, approximately a teaspoonful of beads for the cell pulverization were put in each of the tubes, and the tubes were attached to "Beads Homogenizer Model BC-20 (available from CENTRAL SCIENTIFIC COMMERCE, INC.)". Subsequently, a rotation axis of the homogenizer was rotated at a rotation speed of 2500 rpm for three minutes, whereby cell walls of the yeast cells were pulverized.

1-2) Treatment for Autolysis

Temperature of an incubator was set to 50° C., and the tubes of Sample Nos. 4~7 and Sample Nos. 10~13, among Sample Nos. 1~13, which contained the yeasts which were subjected to the above treatment of cell destruction, were accommodated in the incubator, and the tubes were kept in the incubator for 24 hours or 48 hours, as shown in TABLE 1 below, whereby autolysis of the yeasts was effected.

1-3) Enzyme-treatment

To the yeasts of Sample Nos. 3, 5, and 7, for which the electrolyzed acidic water was used, there was added an acidic protease in an amount which corresponds to 1% of a weight of the yeast body. Meanwhile, to the yeasts of Sample Nos. 9, 11, and 13, for which the electrolyzed alkaline water was used, there was added an alkaline protease in an amount which corresponds to 0.5% of a weight of the yeast body. These samples were placed in an incubator whose temperature was set to 60° C., which was an optimum temperature of the added yeasts, and the samples were kept in the incubator for two or four hours, whereby the yeasts were enzyme-treated. In this treatment, there was adopted "Protease M" (available from AMANO ENZYME INC.) as the acidic protease, while there was adopted "Proleser-FG-F" (available from AMANO ENZYME INC.) as the basic protease. To Sample Nos. 5, 7, 11, and 13, in which the autolysis of the yeasts was effected as described above, the enzyme was added immediately after the autolysis of yeasts was effected, whereby the yeasts were enzyme-treated.

1-4) Confirmation Test for Digestion of the Protein

After the above-mentioned treatments, Sample Nos. 1~13 were sufficiently stirred and blended, so that only the beads were precipitated. Each of thus obtained sample solutions as it was, without being diluted, was mixed with a sample buffer for the SDS-PAGE (CBB solution) in a ratio of 1:1, and there was caused a reaction at 100° C. for five minutes. Subsequently, 15 μl of each of samples was applied to each of lanes, and then a 200V charge was applied to the gel, whereby the protein was migrated by the SDS-PAGE. Then, photographs which indicated results of the SDS-PAGE were shown in FIGS. 1 (a) and (b). Also, degrees of staining of the gel (degrees of strength of blue color) were classified into five grades by using a symbol "+", and the results were indicated in TABLE 1 and FIG. 1 below. In this case, the deeper the color was, more symbols "+" were given, which indicated that digestibility (degradation rate) of the protein was poor.

In FIGS. 1(a) and (b), results of the tests of the samples, which were enzyme-treated, are separately shown, depending on the time of the enzyme-treatment, i.e., two hours or four hours. Meanwhile, results of the tests of the samples, which were not enzyme-treated, are shown in both FIGS. 1(a) and (b).

TABLE 1

| No. | Medium | Autolysis | Enzyme-treatment | Evaluation |
|---|---|---|---|---|
| 1 | Distilled water | None | None | +++++ |
| 2 | Electrolyzed acidic water (pH 4.11) | None | None | +++++ |
| 3 | Electrolyzed acidic water (pH 4.11) | None | 2 hours<br>4 hours | ++++<br>++++ |
| 4 | Electrolyzed acidic water (pH 4.11) | 24 hours | None | +++ |
| 5 | Electrolyzed acidic water (pH 4.11) | 24 hours | 2 hours<br>4 hours | +++<br>++ |
| 6 | Electrolyzed acidic water (pH 4.11) | 48 hours | None | +++ |
| 7 | Electrolyzed acidic water (pH 4.11) | 48 hours | 2 hours<br>4 hours | +++<br>++ |
| 8 | Electrolyzed alkaline water (pH 9.72) | None | None | +++++ |
| 9 | Electrolyzed alkaline water (pH 9.72) | None | 2 hours<br>4 hours | ++++<br>++++ |
| 10 | Electrolyzed alkaline water (pH 9.72) | 24 hours | None | +++ |
| 11 | Electrolyzed alkaline water (pH 9.72) | 24 hours | 2 hours<br>4 hours | +++<br>++ |
| 12 | Electrolyzed alkaline water (pH 9.72) | 48 hours | None | +++ |
| 13 | Electrolyzed alkaline water (pH 9.72) | 48 hours | 2 hours<br>4 hours | ++<br>+ |

Figure 1B:
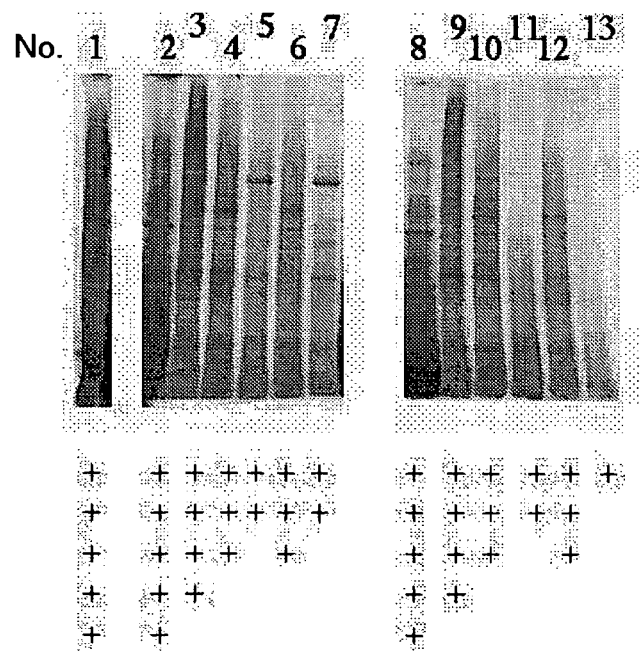

As it is apparent from TABLE 1 and FIG. 1, there is recognized that enhanced digestibility is observed in the Sample Nos. 11 and 13, in which the yeasts were enzyme-treated with the basic protease after the yeasts were autolyzed in the electrolyzed alkaline water.

On the contrary, in Sample Nos. 5 and 7, of which the yeasts were enzyme-treated in the electrolyzed acidic water, there are observed particular bands, and recognized that the yeast protein cannot be sufficiently degraded and removed, even if the acidic protease is used in the electrolyzed acidic water which has a high oxidizability.

Also, as it is apparent from the results of the Sample No. 12, of which only the autolysis of the yeast is effected for 48 hours, there is recognized that if the yeast is only autolyzed with the intracellular enzyme thereof, there is a limitation in removal of the protein.

Example 2

There was produced a β-glucan by adopting the conditions of effecting the autolysis and the enzyme-treatment of Sample No. 13, which exhibited the most preferable results in the above EXAMPLE 1. In detail, after a sample was prepared by adding 50 g of the dry yeast to 500 ml of the electrolyzed alkaline water (pH=10.0), yeast cells were pulverized by using a ball mill. Subsequently, thus pulverized yeast was autolyzed by being kept in an incubator at 50° C. for 48 hours, and then a basic protease (Proleser-FG-F) was added to the sample, in an amount which corresponds to 0.5% of a weight of the yeast body, and the sample was kept in the incubator at 60° C. for four hours, whereby the yeast of the sample was enzyme-treated. Thereafter, the sample was heat-treated for 10 minutes by using a boiling water, so that the enzyme in the electrolyzed alkaline water was inactivated, and then the sample was centrifuged, and a supernatant thereof was removed. Subsequently, 500 ml of the electrolyzed alkaline water (pH=10.0) was added to the sample, and the sample was agitated, whereby the sample was suspended. Further, a rinsing-treatment, in which the sample was centrifuged and a supernatant thereof was removed, was repeated for three times. Thereafter, 500 ml of distilled water was added to the sample, and the sample was suspended, and then the sample was centrifuged and a supernatant thereof was removed, whereby a precipitate was obtained. Subsequently, a suitable amount of distilled water was added to thus obtained precipitate, and then the precipitate, to which the distilled water was added, was transferred to another container and was freeze-dried in the container. In this way, the yeast-derived β-glucan was produced.

Figure 2A:
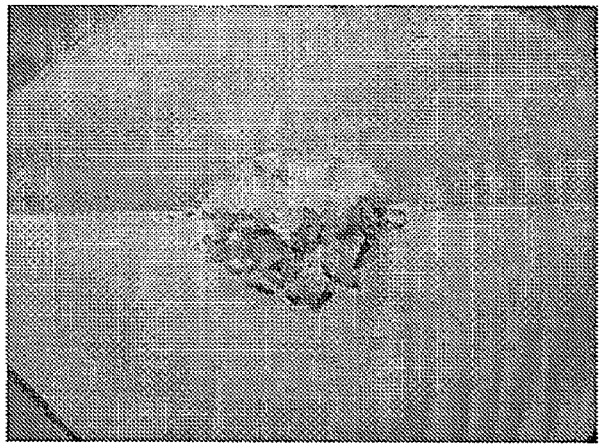
Figure 2B:
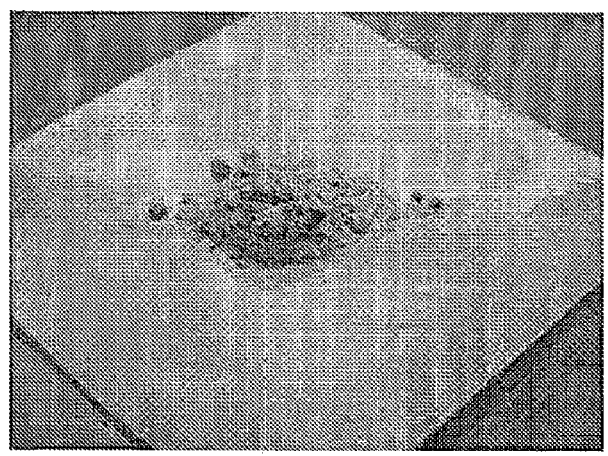
Figure 3A:
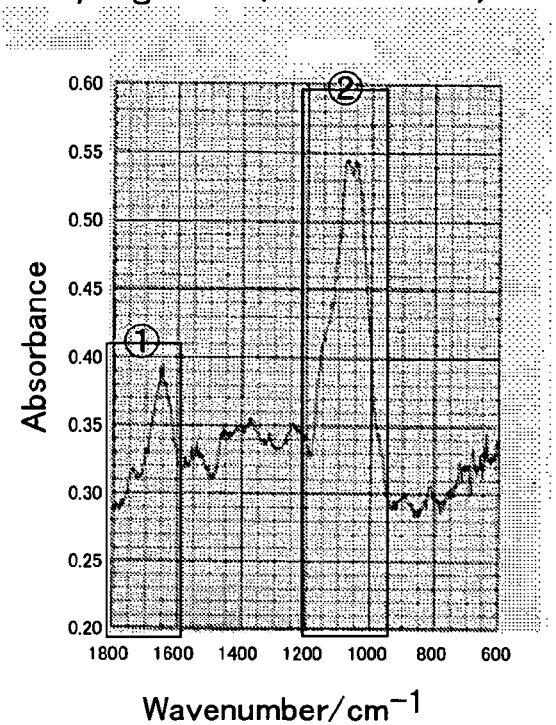
FIGS. 3a and 3b are waveform charts of the glucan, wherein FIG. 3a indicates FTIR spectrum of the β-glucan produced in EXAMPLE 2, while FIG. 3b indicates FTIR spectrum of a standard product.
Figure 3B:
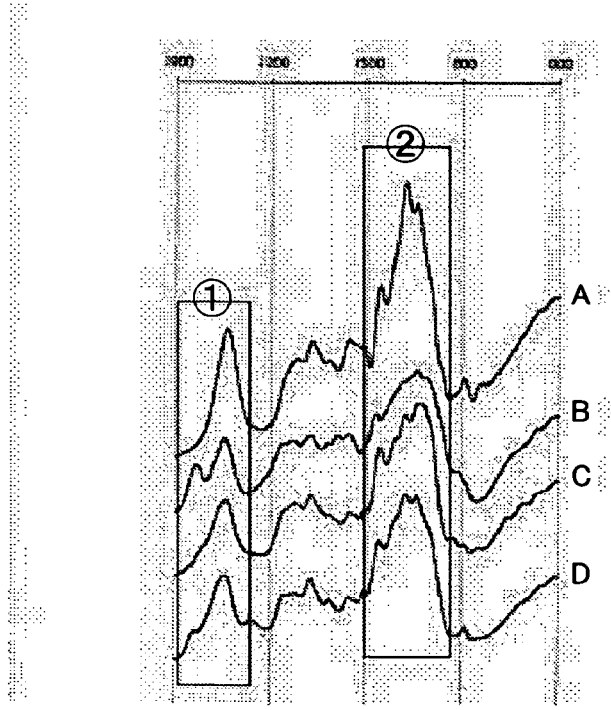

FIG. 2(a) shows a photograph of the β-glucan extracted from the yeast plant as described above, and FIG. 2(b) shows a photograph of a commercially available β-glucan, for the sake of comparison. Also, the obtained β-glucan was analyzed by Fourier transform infrared spectroscopy (FTIR), and a chart obtained by the analysis is shown in FIG. 3(a). In FIG. 3(b), there are also shown charts of four standard products (A: β-1,3-glucan, B: β-1,6-glucan, C: glucan extracted from the brewer's yeast, D: cell wall of the baker's yeast), for the sake of comparison,. (See P. Thanardkit, P. Khunrae, M. Suphantharika and C. Verduyn, Glucan from spent brewer's yeast: preparation, analysis and use as a potential immunostimulant in shrimp feed. World Journal of Microbiology & Biotechnology, Vol. 18, 527-539, 2002).

The commercially available glucans degrade the lipid and the protein by a hydrolysis by using a strong alkali or acid, so that the glucans are colored or have an oxidation off-flavor because of the oxidation etc. of the lipid. On the other hand, the β-glucan produced as described above has a whiteness and has no flavor. There is estimated that these are caused by an act of a reducing power by the electrolyzed alkaline water, so that the lipid and the glucan included in the yeast were not oxidized, and there is exhibited an act of a reduction bleaching by the electrolyzed alkaline water.

Ranges indicated by ① and ② in FIGS. 3(a) and (b) are wavelength windows of waveforms, which are characteristics of the β-glucan. By comparing thus obtained FTIR spectra of the β-glucan with FTIR spectra of a standard product, there can be recognized, based on the waveform of the obtained glucan, the obtained glucan is a mixture of β-1,6-glucan which mainly comprises β-1,3-glucan. In addition, there is not seen an excessive peak, so that there can be assumed that the obtained glucan has a considerably high purity. Further, there was calculated a yield of the β-glucan extracted from the yeast, and found that the yield was about 5%.

Example 3

3-1) Treatment for Pulverizing Yeast Cells 0.05 g of the dry yeast was measured and accommodated in each of tubes for pulverizing cells. Then, 0.5 ml of an electrolyzed alkaline water (pH 9.95) was added to each of the tubes. Also, an alkaline protease ("Proleser-FG-F") was added to each of the tubes, in an amount which corresponds to a percentage as shown in TABLE 2 below. Thereafter, about a teaspoonful of beads for pulverizing the cells was put into each of the tubes, and cell walls of the yeast cells were pulverized, similar to EXAMPLE 1.

3-2) Treatment for Autolysis and Enzyme-treatment

The yeasts of Sample Nos. 14~25, which were subjected to the above-mentioned treatment for pulverizing cells, were kept at 55° C., which was close to the optimum temperature of the added enzyme, for the respective time indicated in TABLE 2 below (0, 2, 4 or 8 hours). In this way, autolysis of the yeasts was effected with the intracellular enzyme thereof and were enzyme-treated.

3-3) Confirmation Test of Digestion of the Protein

Figure 4:
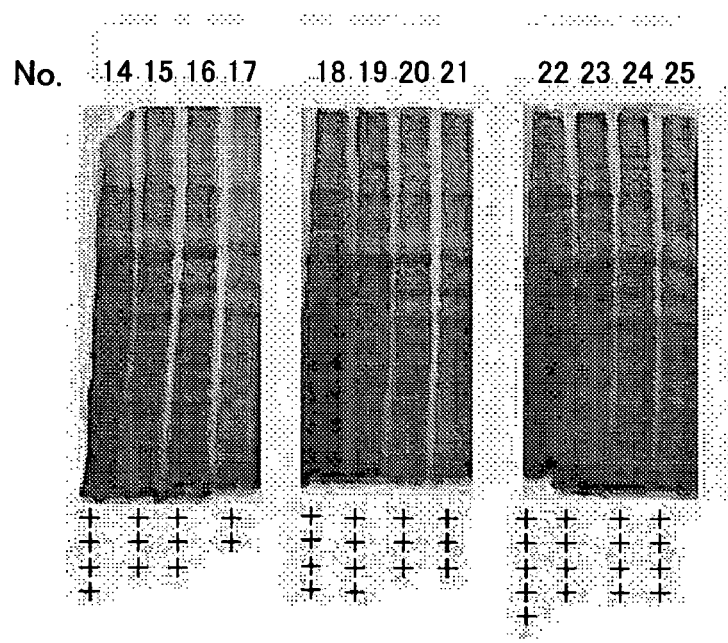
FIG. 4 is a figure showing results of the SDS-PAGE of EXAMPLE 3, wherein degrees of strength of blue color of the gel are indicated by the number of "+", together with photographs of the gel after the electrophoresis.

In Sample Nos. 13~25, there were caused migrations of the protein by the SDS-PAGE, similar to the above EXAMPLE 1, and photographs, which indicated the results, were shown in FIG. 4. There were also evaluated degrees of staining (degrees of strength of blue color), similar to the above EXAMPLE 1, and the results were indicated in TABLE 2 below and FIG. 4.

TABLE 2

| No. | Medium | Percentage of added enzyme* | Time of autolysis/ enzyme- treatment | Evaluation |
|---|---|---|---|---|
| 14 | Electrolyzed alkaline water (pH 9.95) | 0.5% | 0 hour | ++++ |
| 15 | Electrolyzed alkaline water (pH 9.95) | 0.5% | 2 hours | +++ |
| 16 | Electrolyzed alkaline water (pH 9.95) | 0.5% | 4 hours | +++ |
| 17 | Electrolyzed alkaline water (pH 9.95) | 0.5% | 8 hours | ++ |
| 18 | Electrolyzed alkaline water (pH 9.95) | 0.1% | 0 hour | ++++ |
| 19 | Electrolyzed alkaline water (pH 9.95) | 0.1% | 2 hours | ++++ |
| 20 | Electrolyzed alkaline water (pH 9.95) | 0.1% | 4 hours | +++ |
| 21 | Electrolyzed alkaline water (pH 9.95) | 0.1% | 8 hours | +++ |
| 22 | Electrolyzed alkaline water (pH 9.95) | 0.05% | 0 hour | +++++ |
| 23 | Electrolyzed alkaline water (pH 9.95) | 0.05% | 2 hours | ++++ |
| 24 | Electrolyzed alkaline water (pH 9.95) | 0.05% | 4 hours | ++++ |
| 25 | Electrolyzed alkaline water (pH 9.95) | 0.05% | 8 hours | ++++ |

*Amount of the added enzyme relative to the weight of the yeast body, which is converted to 100% (for instance, if the percentage is 0.5%, the amount of the added enzyme is 0.5 parts by weight per 100 parts by weight of the yeast body).

As it is apparent from the results in TABLE 2 and FIG. 4, the protein of Sample No. 17, of which the concentration of the oxygen was 0.5% and the treatment time was eight hours, was the most degraded. If the Sample No. 17 is compared with Sample No. 13 of EXAMPLE 1, digestibility of the protein of Sample No. 17 is lower than that of Sample No. 13 of EXAMPLE 1. However, Sample No. 17 after eight hours was evaluated as "++". Therefore, there is assumed that if the treatment time had been a little longer, Sample No. 17 may have provided a digestibility similar to that of Sample No. 13. Accordingly, there is assumed that the protein in the yeast cells can be removed in a shorter period of time, if the autolysis of the yeast is effected with the intracellular enzyme thereof and simultaneously enzyme-treated with the added enzyme, whereby the production time of the glucan can be reduced.

Example 4

4-1) Treatment for Pulverizing Yeast Cells 0.05 g of the dry yeast was measured and accommodated in each of tubes for pulverizing cells. Then, 0.5 ml of the electrolyzed alkaline water (pH=9.72) was added to each of the tubes. Thereafter, about a teaspoonful of beads for pulverizing the cells was put into each of the tubes. Subsequently, cell walls of the yeast cells were pulverized, similar to EXAMPLE 1.

4-2) Heat-treatment

Sample Nos. 26 and 27, which were subjected to the above treatment for pulverizing the cells, were heated at 95° C. for five minutes, whereby the intracellular enzymes of the yeasts were inactivated. Subsequently, Sample Nos. 26 and 27 were centrifuged at a rotation speed of 13,000 rpm for five minutes, and a supernatant thereof was removed. Thereafter, another 0.5 ml of the electrolyzed alkaline water (pH=9.72) was added to each of Sample Nos. 26 and 27, and each of the samples were well agitated.

4-3) Enzyme-treatment

To Sample No. 27, which was one of the samples subjected to the above heat-treatment, an alkaline protease ("Proleser-FG-F") was added, in an amount corresponding to 0.5% of the weight of the yeast body. Then, Sample No. 27 was kept at 55° C., which was close to the optimum temperature of the added enzyme, for four hours. In this way, there was effected the enzyme-treatment with the added enzyme.

4-4) Confirmation Test of Digestion of the Protein

Figure 5:
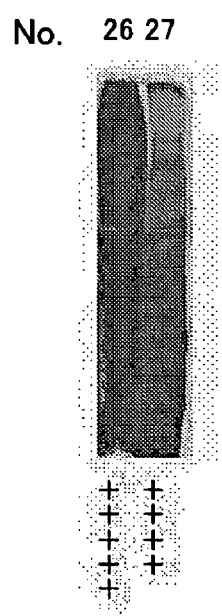
FIG. 5 is a figure showing results of the SDS-PAGE of EXAMPLE 4, wherein degrees of strength of blue color of the gel are indicated by the number of "+", together with photographs of the gel after the electrophoresis.

In Sample Nos. 26 and 27, there were caused migrations of the protein by the SDS-PAGE, similar to the above EXAMPLE 1, and photographs, which indicated the results, were shown in FIG. 5. There were also evaluated degrees of staining (degrees of strength of blue color), similar to the above EXAMPLE 1, and the results were indicated in TABLE 3 below and FIG. 5.

TABLE 3

| No. | Medium | Percentage of added enzyme* | Treatment time | Evaluation |
|---|---|---|---|---|
| 26 | Electrolyzed alkaline water (pH 9.72) | None | — | +++++ |
| 27 | Electrolyzed alkaline water (pH 9.72) | 0.5% | 4 hours | ++++ |

*Amount of the added enzyme relative to the weight of the yeast body, which is converted to 100% (for instance, if the percentage is 0.5%, the amount of the added enzyme is 0.5 parts by weight per 100 parts by weight of the yeast body).

As it is apparent from TABLE 3 and FIG. 5, there was not digested the protein of Sample No. 26, wherein the autolysis and the enzyme-treatment were not effected, although the electrolyzed alkaline water was used.

In Sample No. 27, wherein only the enzyme-treatment in the electrolyzed alkaline water was effected, the protein was denatured by heat, and digestibility of the protein is lower than that of Sample No. 16 of EXAMPLE 3, in which the autolysis and the enzyme-treatment were executed in the electrolyzed alkaline water. This is presumably because intracellular enzyme of the yeast was inactivated by the heat-treatment, and the degradation of the protein by the alkaline protease was interrupted by aggregation and polymerization of the protein caused by the heat denaturation. Therefore, there is assumed that, if there is effected only the enzyme-treatment with the alkaline protease, there is a limitation in removal of the protein.

Example 5

5-1) Treatment for Pulverizing Yeast Cells 0.05 g of the dry yeast was measured and accommodated in each of tubes for pulverizing cells. Then, 0.5 ml of the electrolyzed alkaline water (pH=9.95) was added to each of the tubes. Thereafter, about a teaspoonful of beads for pulverizing the cells was put into each of the tubes. In this way, cell walls of the yeast cells were pulverized, similar to EXAMPLE 1.

5-2) Rinsing-treatment of the Yeast

Among Sample Nos. 28~41, which were subjected to the above treatment for pulverizing the cells, Sample Nos. 29~41, excluding Sample No. 28, were further subjected to a rinsing-treatment. In detail, each of Sample Nos. 29~41 was centrifuged at a rotation speed of 13,000 rpm for five minutes and a supernatant thereof was removed. Subsequently, another 0.5 ml of an electrolyzed alkaline water (pH=9.72) was added to each of Sample Nos. 29~41, and each of the samples was well agitated. In this way, the yeasts of the samples were rinsed.

5-3) Treatment for Autolysis and Enzyme-treatment

To each of Sample Nos. 30~41, which were among the samples subjected to the above-mentioned rinsing-treatment, an alkaline protease ("Proleser-FG-F") was respectively added in an amount, which corresponds to a percentage as shown in TABLE 4 below. Then, Sample Nos. 30~41 were kept at 55° C., which was close to the optimum temperature of the added enzyme, for the respective time indicated in TABLE 2 below (0, 2, 4 or 8 hours). In this way, the autolysis of the yeasts was effected with the intracellular enzyme of the yeast and enzyme-treated with the added enzyme.

5-4) Confirmation Test for Digestion of the Protein

Figure 6:
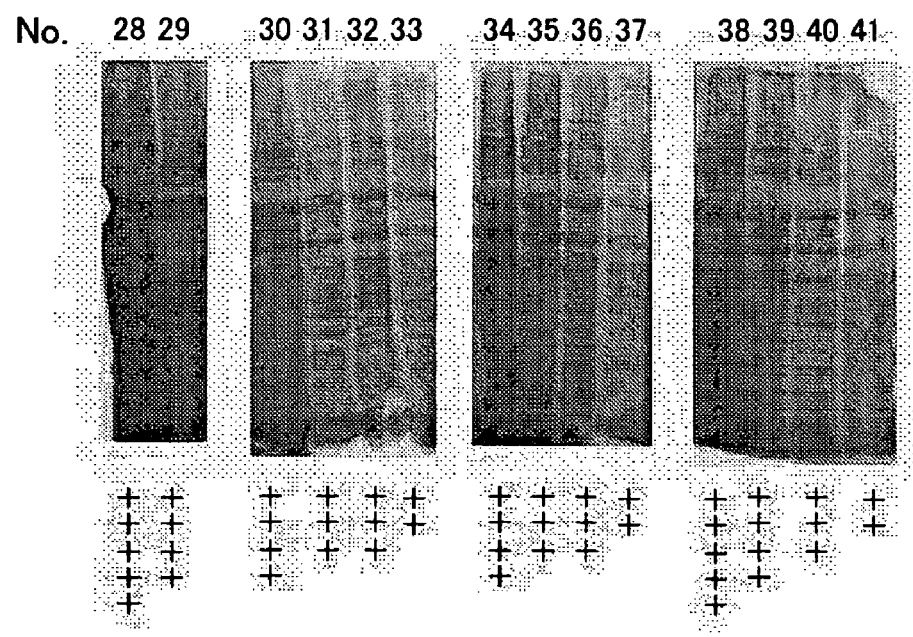
FIG. 6 is a figure showing results of the SDS-PAGE of EXAMPLE 5, wherein degrees of strength of blue color of the gel are indicated by the number of "+", together with photographs of the gel after the electrophoresis.

In Sample Nos. 28~41, there were caused migrations of the protein by the SDS-PAGE, similar to the above EXAMPLE 1, and photographs, which indicated the results, were shown in FIG. 6. There were also evaluated degrees of staining (degrees of strength of blue color), similar to the above EXAMPLE 1, and the results were indicated in TABLE 4 below and FIG. 6.

TABLE 4

| No. | Medium | Rinsing-treatment | Percentage of added enzyme* | Treatment time | Evaluation |
|---|---|---|---|---|---|
| 28 | Electrolyzed alkaline water (pH 9.95) | No | None | None | +++++ |
| 29 | Electrolyzed alkaline water (pH 9.95) | Yes | None | None | ++++ |
| 30 | Electrolyzed alkaline water (pH 9.95) | Yes | 0.5% | 0 hour | ++++ |
| 31 | Electrolyzed alkaline water (pH 9.95) | Yes | 0.5% | 2 hours | +++ |
| 32 | Electrolyzed alkaline water (pH 9.95) | Yes | 0.5% | 4 hours | +++ |
| 33 | Electrolyzed alkaline water (pH 9.95) | Yes | 0.5% | 8 hours | ++ |
| 34 | Electrolyzed alkaline water (pH 9.95) | Yes | 0.1% | 0 hour | ++++ |
| 35 | Electrolyzed alkaline water (pH 9.95) | Yes | 0.1% | 2 hours | +++ |
| 36 | Electrolyzed alkaline water (pH 9.95) | Yes | 0.1% | 4 hours | +++ |
| 37 | Electrolyzed alkaline water (pH 9.95) | Yes | 0.1% | 8 hours | ++ |
| 38 | Electrolyzed alkaline water (pH 9.95) | Yes | 0.05% | 0 hour | +++++ |
| 39 | Electrolyzed alkaline water (pH 9.95) | Yes | 0.05% | 2 hours | ++++ |
| 40 | Electrolyzed alkaline water (pH 9.95) | Yes | 0.05% | 4 hours | +++ |
| 41 | Electrolyzed alkaline water (pH 9.95) | Yes | 0.05% | 8 hours | ++ |

*Amount of the added enzyme relative to the weight of the yeast body, which is converted to 100% (for instance, if the percentage is 0.5%, the amount of the added enzyme is 0.5 parts by weight per 100 parts by weight of the yeast body).

As it is apparent from the results in TABLE 4 and FIG. 6, the amount of the protein included in Sample No. 29, in which the yeast was rinsed, is less than that of Sample No. 28, in which the yeast was not rinsed. This is probably because a part of the protein, which had been dissolved in the electrolyzed alkaline water, was swept by rinsing. Meanwhile, there is not observed a significant difference between Sample Nos. 30~41, which were subjected to the rinsing-treatment, and Sample Nos. 14~25, which were not subjected to the rinsing-treatment. However, the electrolyzed alkaline water has an effect of dissolving the protein, although the amount is little, and has an effect of removing impurities, such as lipid, so that the rinsing-treatment is assumed to be effective.

What is claimed is:

1. A process for producing a yeast-derived glucan, comprising:
    autolyzing a physically pulverized yeast with an intracellular enzyme thereof, in an electrolyzed alkaline water having a pH within a range of 8.5-11.5 obtained by electrolyzing water, while the yeast is enzyme-treated by adding an alkaline protease to the yeast to produce said glucan, wherein said process is carried out in the absence of a hydroxide of an alkali metal.

2. The process for producing a yeast-derived glucan according to claim 1, wherein the yeast is physically pulverized in the electrolyzed alkaline water.

3. The process for producing a yeast-derived glucan according to claim 1, wherein an oxidation-reduction potential of the electrolyzed alkaline water is within a range of −100-−800 mV.

4. The process for producing a yeast-derived glucan according to claim 1, wherein a temperature for the autolysis is within a range of 40° C.-70° C.

5. The process for producing a yeast-derived glucan according to claim 1, wherein a time for the autolysis is within a range of 8-48 hours.

6. The process for producing a yeast-derived glucan according to claim 1, wherein a temperature for the enzyme-treatment is within a range of 45° C.-70° C.

7. The process for producing a yeast-derived glucan according to claim 1, wherein a time for the enzyme-treatment is within a range of 1-48 hours.

8. A process for producing a yeast-derived glucan, comprising the steps of:
    preparing a mixture by adding a yeast and an alkaline protease to an electrolyzed alkaline water having a pH within a range of 8.5-11.5, wherein the electrolyzed alkaline water is obtained by electrolyzing water;
    physically pulverizing the yeast in thus obtained mixture; and
    autolyzing the yeast with an intracellular enzyme thereof, and simultaneously enzyme-treating the yeast with the alkaline protease to produce said glucan, wherein said process is carried out in the absence of a hydroxide of an alkali metal.

9. The process for producing a yeast-derived glucan according to claim 8, wherein an oxidation-reduction potential of the electrolyzed alkaline water is within a range of −100-−800 mV.

10. The process for producing a yeast-derived glucan according to claim 8, wherein a temperature for the autolysis is within a range of 40° C.-70° C.

11. The process for producing a yeast-derived glucan according to claim 8, wherein a time for the autolysis is within a range of 8-48 hours.

12. The process for producing a yeast-derived glucan according to claim 8, wherein a temperature for the enzyme-treatment is within a range of 45° C.-70° C.

13. The process for producing a yeast-derived glucan according to claim 8, wherein a time for the enzyme-treatment is within a range of 1-48 hours.

14. A process for producing a yeast-derived glucan, comprising:
adding an alkaline protease for an enzyme treatment to a physically pulverized yeast in an electrolyzed alkaline water having a pH within a range of 8.5- 11.5 obtained by electrolyzing water, wherein said protease is added immediately after the yeast is physically pulverized, so that autolysis of the yeast with an intracellular enzyme thereof and enzyme-treatment are simultaneously effected to produce said glucan, wherein said process is carried out in the absence of a hydroxide of an alkali metal.

15. The process for producing a yeast-derived glucan according to claim 14, wherein an oxidation-reduction potential of the electrolyzed alkaline water is within a range of −100-−800 mV.

16. The process for producing a yeast-derived glucan according to claim 14, wherein a temperature for the autolysis is within a range of 40° C.-70° C.

17. The process for producing a yeast-derived glucan according to claim 14, wherein a time for the autolysis is within a range of 8-48 hours.

18. The process for producing a yeast-derived glucan according to claim 14, wherein a temperature for the enzyme-treatment is within a range of 45° C.-70° C.

19. The process for producing a yeast-derived glucan according to claim 14, wherein a time for the enzyme-treatment is within a range of 1-48 hours

* * * * *